United States Patent [19]

Christensen

[11] Plant 4,355

[45] Dec. 26, 1978

[54] MINIATURE MOSS ROSE PLANT

[75] Inventor: Jack E. Christensen, San Dimas, Calif.

[73] Assignee: Armstrong Nurseries, Inc., Ontario, Calif.

[21] Appl. No.: 864,244

[22] Filed: Dec. 27, 1977

[51] Int. Cl.[2] ..... A01H 5/00
[52] U.S. Cl. ..... Plt./9
[58] Field of Search ..... Plt./9

*Primary Examiner*—Robert E. Bagwill
*Attorney, Agent, or Firm*—Andrew R. Klein

[57] ABSTRACT

A new variety of hybrid miniature moss rose, bearing many moss-scented stipitate glands on its stems, peduncles, buds and sepals. The plant grows vigorously, is hardy, and blooms almost continuously throughout the growing season. It is fairly large, in comparison to roses of the miniature class generally. Its blooms are medium pink in color, and have very double petalage, with from 25 to 60 petals and from 1 to 8 petaloids. It has viable pollen and will set hips when grown under greenhouse conditions. It has a better-than-average resistance to mildew, as compared to other roses of its class, grown under parallel conditions.

1 Drawing Figure

This invention relates to a hybrid miniature moss rose of the hardy dwarf type. The plant is a bush outdoor seedling cultivated primarily for cut flowers and garden decoration. For purposes of varietal identification, it has been given the denomination of "ARODI".

The seed parent was "Fairy Moss" (U.S. Plant Pat. No. 3,083) and the pollen parent was "Iceberg". The plant was first produced in Ontario, California, and the descriptive and comparative references to this plant and its bloom hereinafter will relate to plants of the same class grown in this region. This variety preserves its distinguishing characteristics through succeeding propagations, by cuttings and budding.

This new variety is most readily distinguished from its seed parent, Fairy Moss, first by the fact that the new rose is very vigorous and grows to a plant size and habit considered to be relatively large in relation to miniature roses generally. In fact, it reaches a mature plant height of about twice the mature height of its seed parent. Secondly the new rose is double to very double in its petalage, having between 25 and 60 petals plus several additional petaloids, while its seed parent is semi-double, having fewer than 25 petals.

The new variety differs from its pollen parent, Iceberg, most notably in the following respects. The new rose is a hybrid miniature moss rose bearing many moss-scented stipitate glands on its stems, peduncles, sepals and buds, while its pollen parent, with comparatively glabrous stems, peduncles and sepals, lacks this "mossy" distinction. The new rose bears flowers ranging from 3 to 4 cm in size, and is of medium pink color as hereinafter described, whereas Iceberg produces white flowers which are approximately twice the size of the new rose. Furthermore, the new rose is miniature in plant habit and growth and reaches a mature height approximately only half the height of its Floribunda parent, Iceberg.

The flowers are usually borne singly, but sometimes three or more to the stem on normal, short to medium-length stems. The plant blooms abundantly outdoors, and almost continuously during the growing season. The blooms, in open flower, have a slight tea fragrance.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

FLOWER

Bud

The peduncle is average length and average caliper, being erect, with numerous scented stipitate glands and numerous small prickles. The color is between Strong Yellow Green, 5GY7/10, and Strong Yellow Green, 5GY6/8.

Before the calyx breaks, the bud is what is considered medium size for miniature roses, medium length, pointed and ovoid in form, with a conspicuous neck. On the surface of the bud, there is moss in the form of highly scented stipitate glands, and usually there are small foliaceous parts extending beyond the tip of the bud for a distance equal to one-quarter or more of its length.

As the calyx breaks, the color is between Deep Purplish Pink, 7.5RP6/12, and Strong Purplish Red, 7.5RP4/11. The inner surface of the sepals carries a fine tomentum, and margins are lined with stipitate glands and/or hairs.

As the first petal opens, the bud is average in size for miniature roses, medium length to long and ovoid to urn-shaped in form. The color on the outside of the petal is between Strong Purplish Pink, 7.5RP7/10, and Strong Purplish Pink, 5RP7/9, with a small area near the base between white and Brilliant Yellow Green, 2.5GY9/8. The inside surface of the petal is between Deep Purplish Pink, 7.5RP6/12, and Strong Purplish Red, 7.5RP5/12, while a small area near the base is the same coloration as on the outside of the petal. The bud opens up well and is not retarded or prevented from opening by cold, hot, wet, or dry weather.

Bloom

The size of the bloom when fully open is average for miniature roses, being from 3 to 4 centimeters in diameter. Petalage is double to very double, quite variable, and ranging usually from 25 to as many as 60 petals, plus 1 to 8 petaloids arranged regularly. The bloom is high centered at first, becoming flat to open to high centered.

At first the petals are somewhat tightly cupped, with tips reflexed outward, becoming later at maturity more loosely cupped, with tips reflexed outward and lateral margins along the lower half of the petals sometimes rolled slightly inward.

PETALS

The petals are of medium thickness, moderately leathery, with inside satiny to velvety and outside slightly shiny to satiny. The outside petals are broadly obovate, while both the intermediate and inside petals are obovate. The colors may be modified by being shaded and/or washed with other colors.

The paragraph immediately following describes color values observed in a flower newly opened in the month of August. The plant had been grown outdoors, in Ontario, Calif.

The outer surfaces of all petals, outside, intermediate and inside, were all essentially the same in coloration, being between Strong Purplish Pink, 7.5RP7/10, and Deep Purplish Pink, 5RP6/10, with a small off-white area near the base. The inner surfaces of all petals were essentially the same, being near Deep Purplish Pink, 7.5RP6/12, also with a small off-white area near the base.

The paragraph immediately following describes color values observed in a bloom which had been open for three days, outdoors, in the month of August. The plant had been grown outdoors, in Ontario, Calif.

The outer surface of both the outside petal and the inside petal was between Strong Purplish Pink, 7.5RP7/10, and Moderate Purplish Pink, 2.5RP7/8, with a small area near the base being off-white in color. The inner surface of both the outside petal and inside petal was between Deep Purplish Pink, 7.5RP6/12, and Moderate Purplish Pink, 2.5RP7/8, also having a small area near the base which was off-white in color.

The general color effect of the newly opened flower is near Deep Purplish Pink, 7.5RP6/12. After being three days open, the bloom gives a general color effect which is between Deep Purplish Pink, 7.5RP6/12, and Strong Purplish Pink, 7.5RP7/10. The petals drop off cleanly, except for petaloids, and are not particularly affected in this respect by cold, hot, wet or dry weather.

The flower on the bush in the garden persists for from 4 to 5 days in the month of August, in the locality named. Cut roses grown outdoors and kept at living-room temperatures will last from 3 to 4 days in the month of August.

Reproductive organs

The stamens are average in number and arranged regularly about the pistils, a few being mixed with petaloids.

The filaments are of medium length, and between white and Brilliant Greenish Yellow, 7.5Y9/8, in color. Most are with anthers.

The anthers are of medium size, all opening approximately at once. The color of the margins is near Strong Orange Yellow, 7.5YR7/11, while being off-white near the point of attachment of the filament.

There is a moderate amount of pollen which is near Strong Orange Yellow, 7.5YR7/11, in color.

The pistils are approximately 40 in number, this being average for miniatures.

The styles are uneven, of average length, thin caliper, and loosely bunched. They are between white and Brilliant Greenish Yellow, 7.5Y9/8, in color, sometimes with very light reddish pigmentation just below the stigma.

The stigma is near Pale Orange Yellow, 7.5YR9/4, in color.

The ovaries are usually all enclosed in the calyx.

This new variety sets hips in the greenhouse, but does not set hips readily outdoors in Southern California. The hips are average length to long and more or less pear-shaped. At half maturity, their ground color is between Strong Yellow Green, 2.5GY7/10, and Strong Yellow Green, 2.5GY6/8, and beginning to change to near Vivid Yellow, 2.5Y8/12. They are prickly and glandular, with thick, fleshy walls.

The sepals are permanent. They are medium-length and recurved. The color of the sepals is basically the same color as the hip, inside and outside, but the inside is overlaid with white tomentum.

The number of seeds ranges from 1 to 7, which is an average number of seeds for miniatures. They are small to medium in size.

PLANT

Foliage

The compound leaves usually comprise 3 to 7 leaflets. They are from normal to abundant, medium size to large, for miniatures, moderately heavy to somewhat leathery, and glossy. The leaflets are oval to ovate in shape, with apex acute, base obtuse and margin irregularly, but predominantly doubly, serrate.

The mature foliage displays upon its upper surface a color which is between Moderate Olive Green, 5GY4/3, and Grayish Olive Green, 5GY3/2. The under surface is near Moderate Yellow Green, 5GY5/6, but overlaid with grayish bloom.

The young foliage, on its upper surface, is between Moderate Yellow Green, 5GY5/6, and Moderate Olive Green, 2.5GY5/5, in color, and, especially near the margins, lightly overlaid with near Dark Red, 5R3/7. The color of the under surface is between Moderate Yellow Green, 2.5GY5/5, and Moderate Olive, 10Y4/3, and being lightly overlaid with near Dark Red, 5R3/7, which is a darker shade near the margins.

The rachis is average size, grooved on its upper side, with some stipitate glands on the edges. The under side is sparsely prickly and with stipitate glands.

The stipules are from medium-length to long, from narrow to medium-width, with medium-length points turning out at an angle of less than 90°.

The plant displays a more than average resistance to mildew, compared to other commercialized varieties grown under comparable conditions in Ontario, Calif.

Growth

The plant is a dwarf variety, bushy, upright-spreading and much branched. It is on the large side for miniature rose plants. Its growth is very vigorous, with canes which are medium in caliper, for miniatures.

The main stems are near Moderate Olive Green, 5GY4/3, in color. They bear several medium-length large prickles, which are almost straight to hooked slightly downward, with short to medium-length moderately broad bases. There are several small prickles, and both the large and small prickles are between gray and Strong Brown, 5YR4/5, in color. There are no hairs, but several stipitate glands.

The branches are near Moderate Yellow Green, 5GY5/6, in color. They bear several large prickles, which are medium-length to long and almost straight, with short to medium-length moderately broad bases. There are several small prickles, and both the large and small prickles are near Strong Brown, 5YR4/5, in color. There are no hairs, but several stipitate glands.

New shoots have a color between Strong Yellow Green, 5GY6/8, and Moderate Yellow Green, 5GY5/6. They bear several large prickles, medium-length to long and almost straight, with medium-length moderately broad bases. There are several small prickles, and the ground color of both the large and small prickles is near Strong Yellow Green, 5GY6/8, and beginning at the base, overlaid with near Strong Yellowish Pink, 5R7/9. There are no hairs, but many stipitate glands.

I claim:

1. A hybrid miniature moss rose plant substantially as herein illustrated and described, being particularly characterized by a combination of features, including the presence of many moss-scented stipitate glands on its stems, peduncles and sepals, the vigor of its growth habit and its ability to bloom almost continuously throughout the growing season, the very double petalage of its blooms, comprised of from 25 to 60 petals, plus 1 to 8 petaloids, and the generally pink coloration of its blooms.

* * * * *

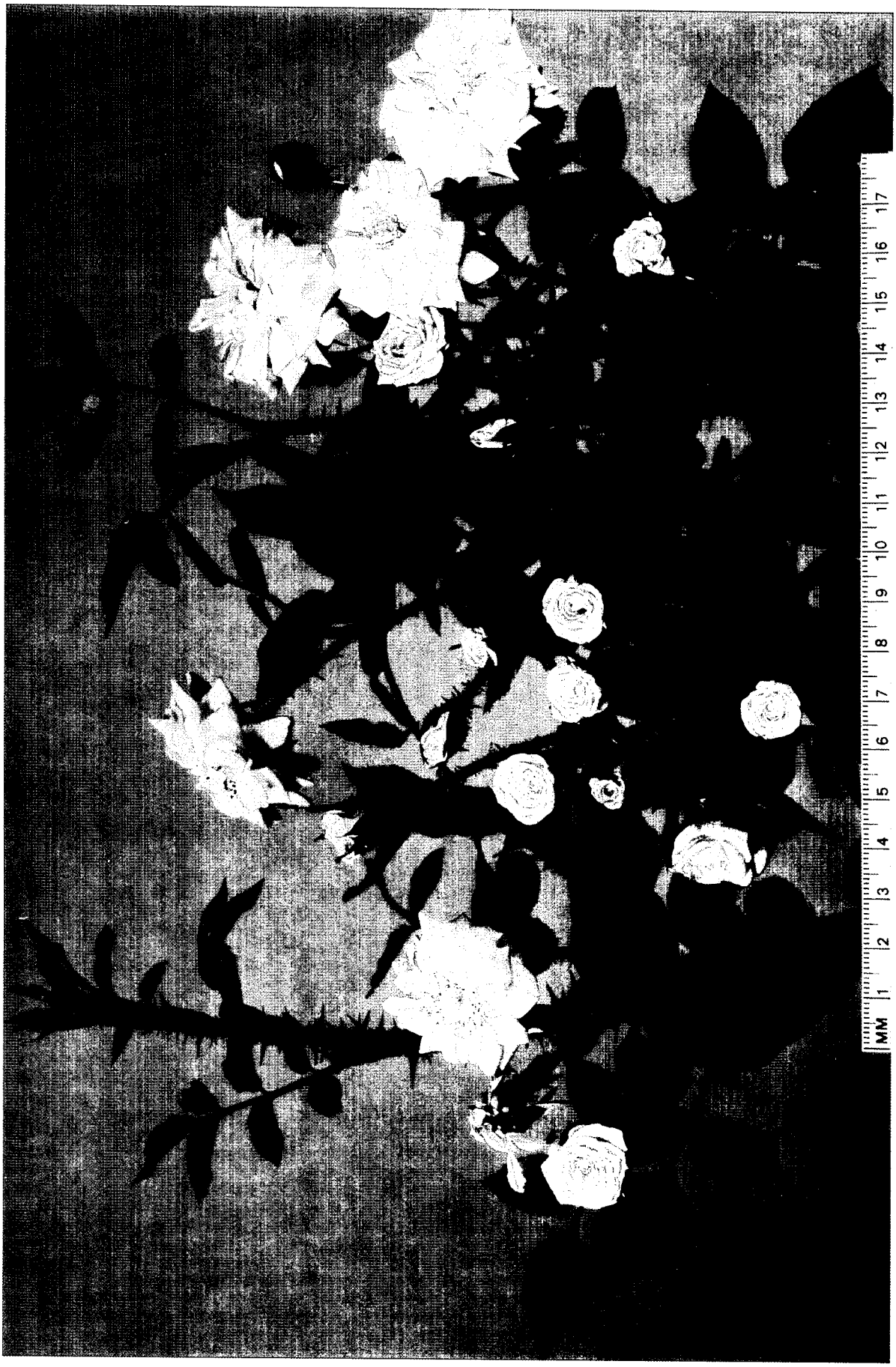
MM
1
2
3
4
5
6
7
8
9
10
11
12
13
14
15
16
17